US006787330B1

(12) United States Patent
Bienvenut et al.

(10) Patent No.: US 6,787,330 B1
(45) Date of Patent: Sep. 7, 2004

(54) METHOD AND KIT FOR IDENTIFYING OR CHARACTERIZING POLYPEPTIDES

(75) Inventors: Willy Vincent Bienvenut, Thenac (FR); Denis Francois Hochstrasser, Geneva (CH); Jean-Charles Sanchez, Geneva (CH)

(73) Assignee: University of Geneva, Geneva (CH)

( * ) Notice: Subject to any disclaimer, the term of this patent is extended or adjusted under 35 U.S.C. 154(b) by 0 days.

(21) Appl. No.: 09/889,711

(22) PCT Filed: Jan. 27, 2000

(86) PCT No.: PCT/EP00/00689

§ 371 (c)(1),
(2), (4) Date: Jul. 18, 2001

(87) PCT Pub. No.: WO00/45168

PCT Pub. Date: Aug. 3, 2000

(30) Foreign Application Priority Data

Jan. 28, 1999 (GB) ............................................. 9901775
Apr. 7, 1999 (GB) ............................................. 9907790

(51) Int. Cl.$^7$ .......................... C12Q 1/37; C12P 21/06; C12N 11/14; C12N 11/02; C12N 11/08
(52) U.S. Cl. ........................ 435/23; 435/68.1; 435/176; 435/177; 435/180; 435/810
(58) Field of Search ........................ 435/23, 68.1, 176, 435/177, 180, 810

(56) References Cited

U.S. PATENT DOCUMENTS

| 4,477,562 | A | 10/1984 | Zeller-Pendrey | 430/513 |
|---|---|---|---|---|
| 5,595,636 | A | 1/1997 | Franzen | 204/464 |
| 5,719,060 | A | 2/1998 | Hutchens et al. | 436/174 |
| 5,783,380 | A | 7/1998 | Smith et al. | 430/619 |
| 6,221,626 | B1 * | 4/2001 | Bienvenut et al. | 435/23 |

FOREIGN PATENT DOCUMENTS

| CA | 2029980 | 11/1990 |
|---|---|---|
| DE | 4408034 | 7/1995 |
| GB | 1502670 | 3/1978 |

OTHER PUBLICATIONS

Hirano, H. et al, Microsequence Analysis of Na Blocked Proteins Electroblotted onto an Immobilizing Matrix from Polyacrylamide Gels. Analytical Sciences, vol. 7 supplement (1991) 941–944.
Cordoba, O.L. et al, "In Gel" Cleavage with Cyanogen Bromide for Protein Internal Sequencing. Biochem. Biophys. Methods, 35, (1997), 1–10.
Fausset, et al, Structural Analysis of Recombinant Proteins Prepared by Semi–Dry Electrobotting After Sodium Dodecyl Sulfate–Polyacrylamide Gels. Electrophoresis Electrophoresis, vol. 12 (1991) 22–27.
Chang et al, Improved Coupling of Proteins to the Support for Solid Phase Protein Sequencing. FEBS Letters, vol. 84 (1) (1977) 187–190.

Jeffcoate et al, Use of Benzamidine to Prevent the Destruction of Thyrotropin–Releasing Hormone (TRH) By Blood. J Chlin Endocrinal Metal., vol. 38 (1974) 155–157.
Aebersold et al, Electroblotting onto Activated Glass. J. Biol. Chem., vol. 2 61 (9) (1986), 4229–4238.
Kussmann et al, Characterisation of the Covalent Structure of Proteins from Biological Material by MALDI Mass Spectrometry—Possibilities and Limitations. Spectroscopy, vol. 14 (1998) 1–27.
Mann et al, Developments in Matrix–Assisted Laser Desorption/Ionization Peptide Mass Spectrometry. Current Opinion in Biotechnology vol. 7 (1996) 11–19.
Roepstorff et al, Mass Spectrometry in Protein Studies from Genome to Function. Current Opinion in Biotechnology vol. 8 (1997) 6–13.
Schevchenko et al, Mass Spectrometric Sequencing of Proteins from Silver–Stalned Polyacrylamide Gels. Anal. Chem., vol68 (1996) 850–858.
M.L. Seo et al, Amperometric Enzyme Electrode for the Determination of NH4+, Journal of the Korean Chemical Society 37 (ii) pp. 937–939 (1993).
K.S. Ha et al, Atmospheric Biosensor for Urea, Bulletin of the Korean Chemical Society 18 (11), pp. 114–115 (1997).
T. Morcal et al, Dot–Blot Analysis of the Degree of Covalent . . . , J. Immunol, Methods 203 (1) 45–53 (1997).
B. Canas et al, Covalent Attachment of Peptides to Membranes . . . , Analytical Biochemistry 211, 179–182 (1993).
C. Viera, Biotechnology Training Program, University of Wisconsin–Madison from http:/www.bact.edu/biotech/vier-a.htm.
J.M. Coull et al., Development of Membrane Supports for the olid–Phase Sequence Anlaysis of Proteins and Peptides, in Methods in Protein Sequence Analysis, Ed. B. Wittman–Lelbold, Springer–Verlag, Berlin (1989), pp. 69–78.
J.M. Coull et al., Functionalized Membrane Support for Covalent Protein Microsequence Analysis, Analytical Biochemistry 194, 110–120 (1991).
MSI Technical Bulletin 633, Transfer of High Molecular Weight proteins from a Non–Denaturing Gel to the MSI PVDF–Plus Membrane (Jun. 19, 1997), from http//www.m-sifilters.com/tb633.txt.
D.J.C. Pappin et al., New Approaches to Covalent Sequence Analysis in Current Research in Protein Chemistry: Techniques,m Structure and Fluction, Ed J.J. Villa–franca, Acad. Press, San Fransisco and London (1990) pp. 191–202.

(List continued on next page.)

Primary Examiner—David M. Naff

(57) ABSTRACT

Polypeptides which have been separated by gel electrophoresis can be identified or characterized by a procedure which has two main stages. In the first stage the gel is digested with a polypeptide-cleaving agent such as an enzyme. This produces mainly large fragments which, in the second stage are electroblotted through a hydrophilic membrane on which is immobilized another polypeptide-cleaving reagent such as an enzyme onto a hydrophobic member, typically a membrane, e.g. of PVDF. The resulting fragments, usually peptides, are identified, preferably by MALDI-TOF MS, or a property may be determined, e.g. by interaction with an antibody.

21 Claims, 9 Drawing Sheets

OTHER PUBLICATIONS

W. Bienvenut et al.., Towards the Automation of Protein Analysis by Mass Spectrometry, Poster P13 and Abstract, Electrophorese Formum '97–Strasbourg (Nov. 25–27, 1997).

Hasselberger, Uses of Enzymes and Immobilized Enzymes, Welson–Hall, Chicago 1978 pp 23, 24 & 29.

Creighton, T.E. Protein Structure a Practical Approach, MCR Laboratory of Molecular Biology, Cambridge, UK.

M. Schreiner et al., Ultraviolet Matrix Assigned Laser Desorption Ionization–Mass Spectrometry of Electroblotted Poteins *Electrophoresis* 17, 954–961 (1996).

\* cited by examiner

IFG digestion

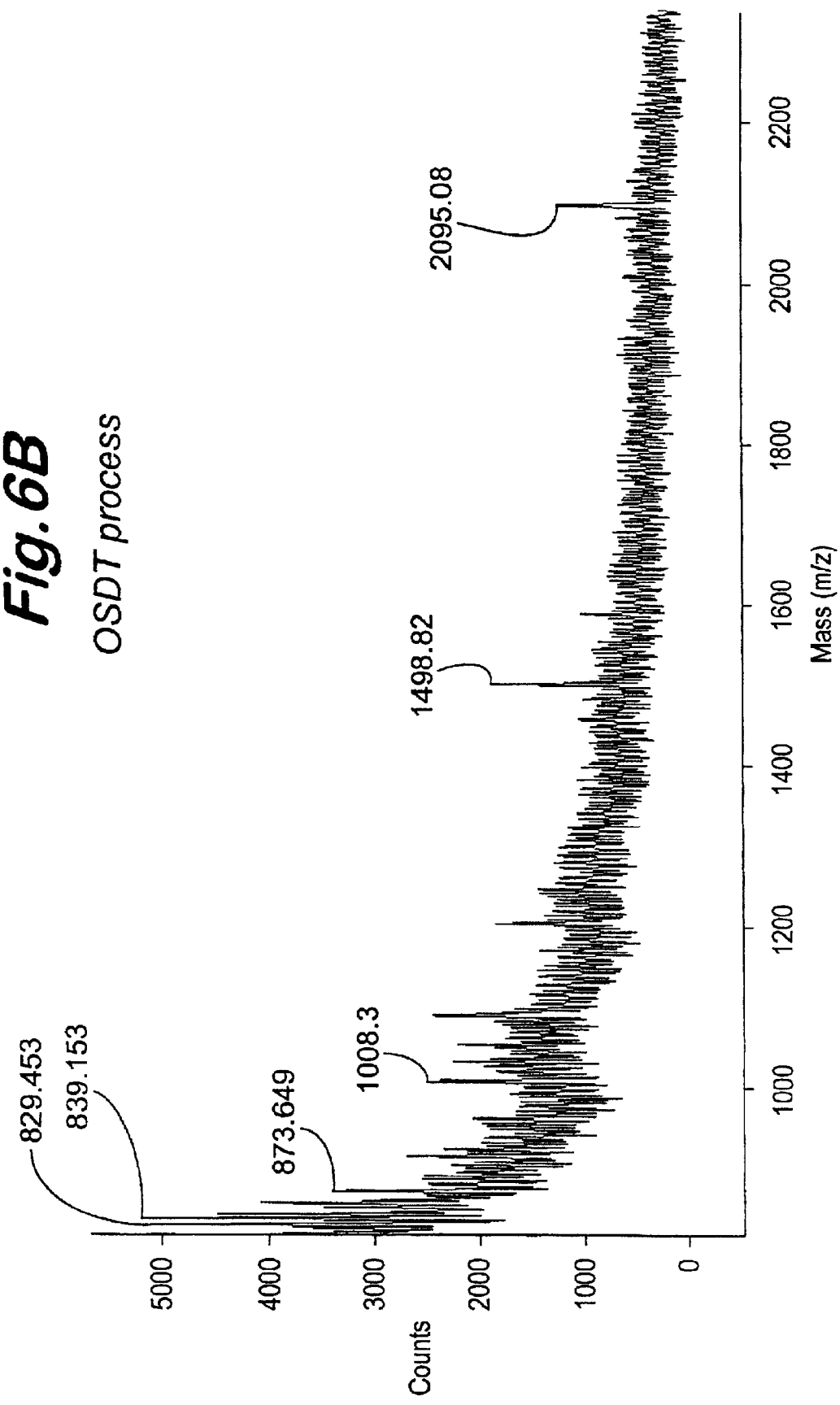

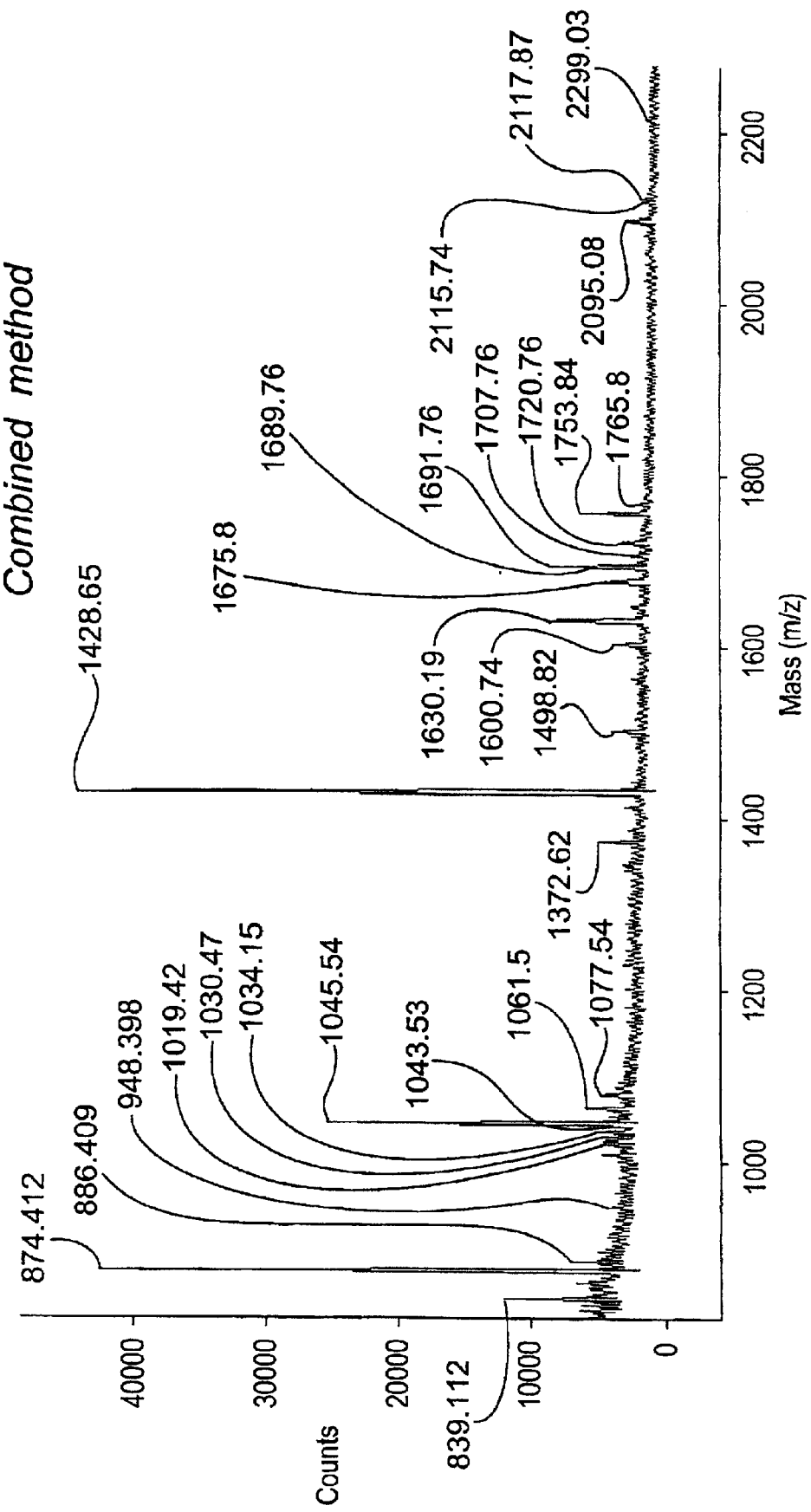
Fig.6C Combined method

*IFG digestion*

OSDT process

Combined method

US 6,787,330 B1

METHOD AND KIT FOR IDENTIFYING OR CHARACTERIZING POLYPEPTIDES

BACKGROUND OF THE INVENTION

1. Field of the Invention

This invention relates to the identification or characterisation of one or more polypeptides which have been isolated on a gel, typically from polyacrylamide gel electrophoresis (PAGE) and to a kit for use in the method. It is especially useful in proteomics (the large scale identification and characterisation of proteins).

2. Description of the Related Art

In proteomics, massively parallel protein identification and characterisation techniques are required. The identification of proteins or other polypeptides merely by PAGE, even using two-dimensional gels (2D-PAGE), is laborious and often uncertain. Many different methods have been developed to identify and partially characterise proteins from complex biological samples. Some of them use Matrix Assisted Laser Desorption/Ionization-Time of Flight Mass Spectrometry (MMI-TOF MS) techniques to analyse peptide "fingerprints" produced by fragmenting the proteins with enzymes. Several software programs have been developed to compare mass spectra of the peptides obtained from MALDI-TOF MS experiments with theoretical spectra from proteins. The subject has been reviewed by M. Kussmann and P. Roepstorff, Spectroscopy 1998, 14, 1–27. These authors noted three ways in which proteins separated by gel electrophoresis could be digested with enzymes to yield fragment peptides:

1. The digestion can be carried out in a plug of excised gel and the peptides recovered by elution. This is the authors' own preference.
2. The protein can be first electroleluted from an excised gel plug and then digested in solution.
3. The protein can be electroblotted onto a membrane and subsequently digested on the membrane.

These types of processes are not practical for the sequencing of polypeptides which have been run on the same gel, since the cutting out of the polypeptide bands from the gel has to be done sequentially and the plugs thus obtained placed in tubes for further analysis. Also, losses occur when the polypeptides adhere to the walls of the tube.

Two of the present inventors have experimented with a different method, which they have termed one-step digestion transfer (OSDT). See U.S. patent application Ser. No. 09/107 991 filed Jun. 30, 1998 and corresponding Canadian Patent Application No. 2 244 947 filed Sep. 24, 1998 entitled "Methods of identifying polypeptides", the disclosure of which is herein incorporated by reference. They have found that the proteins or other polypeptides separated on a gel can be cleaved into fragments, for example by digestion with an enzyme, and that these fragments are presented very satisfactorily for analysis, especially by MALDI-TOF NS, if the cleaving reagent is immobilised on a hydrophilic membrane and interposed as the "filling" in a blotting "sandwich" between the separation gel as one "slice" of the sandwich and a hydrophobic collection member, exemplified as a conventional polyvinylidene fluoride (PVDF) membrane, as the other "slice" of the sandwich. In this way, the fragments are collected on the hydrophobic member and can then be formulated in an appropriate way for the MALDI-TOF MS. It is only necessary that the transblotting is carried out so that the proteins have a long enough residence period in the proximity of the immobilised cleaving reagent to ensure that a reasonable amount of the fragments is produced, but, of course, not so long as to allow undesired diffusion. With electroblotting, i.e. blotting assisted by an electric field, this is easily achievable by varying appropriately the current used in the electroblotting, e.g. by pulsing the current or using a unsymmetrical alternating current. Further, when an enzyme is used as the cleaving agent and when the enzyme is immobilised securely on a hydrophilic membrane, especially by covalent bonding to the solid phase, autodigestion (cleavage of the enzyme by itself) is inhibited.

The OSDT method gives good results for many proteins, but very strongly basic proteins such as lysozyme are not easily transferred under the conditions which are optimal for use of the preferred enzyme, trypsin. Trypsin gives best digestion in a buffer of pH about 8.4. Also, the OSDT method does not give good digestion of very high molecular weight proteins.

SUMMARY OF THE INVENTION

The present invention Is an improvement to the OSDT method and is based in part on the discovery of another technology which the inventors have termed "in full gel digestion" (IFG). This procedure involves dehydrating the gel and then rehydrating it, adding to gel a polypeptide-cleaving reagent such as an enzyme, e.g. in the rehydration buffer. After the IFG, the digested proteins are then electroblotted in a conventional way. One drawback of this technique is the loss of low molecular weight proteins (those of m.w. less than 40 kDa) by diffusion during the in-gel digestions.

It has now been found that by combining the IFG procedure, optionally modified, with OSDT, satisfactory digestion of the proteins (or other polypeptides), accompanied by improved identification, can be achieved for polypeptides having a wide range of molecular weights. Moreover, high molecular weight proteins can be satisfactorily immunoblotted to yield fragments which can be identified as epitopes.

In a preferred "combined procedure", the gel is dehydrated and at least partially, preferably only partially, rehydrated with a buffer containing the polypeptide-cleaving reagent, IFG is performed and this is then followed by OSDT.

In one aspect the invention provides a method of identifying or characterising polypeptides which have been isolated on a gel by electrophoresis, comprising:

a) providing a gel on which at least one polypeptide has been isolated;

b) incorporating a first polypeptide-cleaving reagent in the gel (preferably by dehydrating the gel and at least partially rehydrating it with a buffer containing the polypeptide-cleaving reagent);

c) providing adjacent to the gel at least one hydrophilic membrane on which is immobilised at least one second polypeptide-cleaving reagent;

d) providing a hydrophobic collection member (preferably a membrane) suitable for receiving thereon fragments of polypeptide transferred thereto from the gel by transblotting, preferably by electroblotting, said hydrophobic member being positioned beyond the hydrophilic membrane in a direction of movement of the fragments of polypeptide;

e) transblotting the polypoptide or polypeptides from the full gel, on which the polypeptide or polypeptides were isolated, through the hydrophilic membrane or membranes, under conditions effective to cause it or them to be cleaved into fragments by the second polypeptide-cleaving reagent, to the hydrophobic member; and f) identifying or characterising the fragments collected on the hydrophobic collection layer.

Preferably the method further comprises g) identifying or characterising the polypeptide from which the fragments were derived.

The invention also includes a kit for use in the method of the invention, said kit comprising:

a) a first polypeptide-cleaving reagent suitable for incorporating in an electrophoretic gel;

b) at least one hydrophilic membrane suitable for use in transblotting of polypeptides separated on an electrophoretic gel, the membrane having at least one second polypeptide-cleaving reagent imobilised thereon; and c) a hydrophobic collection member suitable for receiving thereon fragments of the separated polypeptides transferred thereto by transblotting.

Elements b) and c) may be provided as separate components, e.g. in separate containers, or as a pre-formed assembly.

The term "cleaving a polypeptide", as used herein, refers to any step in which a group, residue or any chain of groups or residues is split off from the remainder of the molecule. It includes cleavage in the main chain of amino acids or in a side-chain or of any terminal or side-chain group or residue, e.g. removal of a C-terminal amino acid by carboxypeptidase, N-terminal amino group by an aminopeptidase or a glycosyl side-chain by a glycosidase is included.

The method of the invention requires digestion in the full gel. That is, the method does not include cutting pieces from the gel and digesting the cut pieces in an enzyme.

Reference above to the gel having been dehydrated covers allowing it to become dehydrated merely by standing in air at ambient temperature or taking deliberate steps to dehydrate it. The term "dehydration" includes complete, substantially complete or partial removal of water from the gel.

The term "collection member" as used herein has a broad meaning, since this is not in itself critical to the invention. Considered in isolation, it may be, for example, a self-supporting membrane, film, or plate, or it may be non-self-supporting, e.g. a hydrophobic layer supported on a substrate, e.g. as a coating. It will normally be porous to the blotting buffer, to enable current to be carried to or from the electrode, but may alternatively be the electrode or in direct electrical communication with it.

The term "transblotting", as used herein, covers any operation of transferring the polypeptide fragments to another surface, which, in this invention, is a hydrophobic collection ember. It includes a process of transfer by capillary action or by electroblotting. In this specification, "transblotting" can be part of any blotting procedure applicable to polypeptides, including, for example immunoblotting.

The term "identifying" as used herein is not synonymous with determining the sequence and includes partially identifying the polypeptide. Further, it includes making a tentative identification based on the most probable of a mall number of possibilities.

The term "kit" as used herein includes combinations of the identified components in separate containers and also an assembly of the hydrophilic membrane(s) and hydrophobic collection layer ready for use. The kit may further include, in separate containers, other reagents useful in the method of the invention, e.g. a buffer for rehydrating the gel, a blotting buffer, reagent(s) which assist in the reaction of the enzyme with the polypeptide fragment and so on.

BRIEF DESCRIPTION OF THE DRAWINGS

FIGS. 6A–6C and 7A–7C show the MALDI-TOF MS spectra obtained from myosin and chicken lysozyme respectively, for IFG (6A, 7A), OSDT (6B, 7B) and the combined method of the invention (6C, 7C).

DESCRIPTION OF THE PREFERRED EMBODIMENTS

Figure 1:
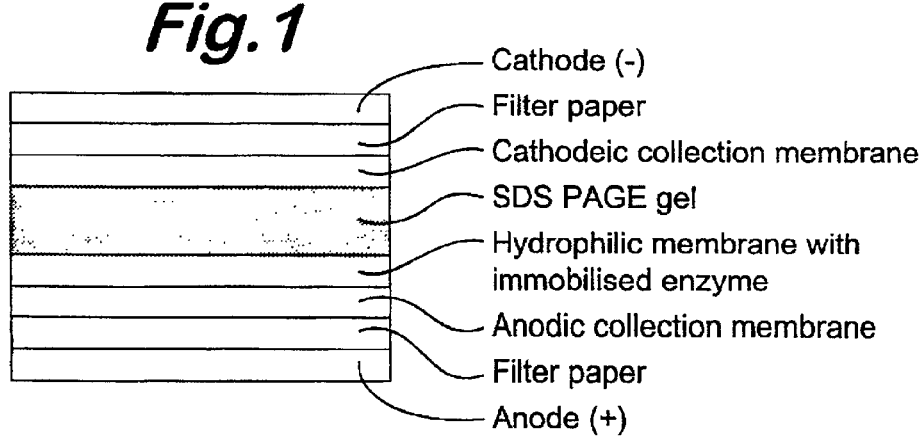
FIGS. 1 and 2 are schematic views of two kinds of blotting "sandwich" which can be used in the invention.

The invention relates to identifying polypeptide(s) which have already been isolated on a gel by gel electrophoresis. The nature of the polypeptide(s) to be identified is not critical. They can be, for example, naturally occurring proteins, proteins made by recombinant DNA technology, polypeptide(s) made by peptide synthesis or by expression of recombinant DNA. For brevity, the invention will be described hereinafter with reference to proteins. The extrapolation to other polypeptide(s) will be taken as understood and incorporated throughout the following description.

The kind of gel on which the proteins have been isolated is not critical, but will usually be a polyacrylamide gel. Any of the conventional gels and separation conditions may have been employed, including reducing conditions. They may be one-dimensional or two-dimensional gels. (In 2D gels, proteins etc. are separated in one dimension by their charge and in the other dimension by their molecular mass).

The invention is normally to be applied to multiple proteins co-present on the same gel, for example from 3 to 3000, more usually 30 to 3000 and preferably 50 to 1500, proteins. This includes proteins present at different molecular weight separations on a 1D gel or at similar molecular weight separations, but present in parallel lanes or tracks on the 1D gel, as well as those separated by 2D gel electrophoresis. However, the invention also applies to a gel on which a single polypeptide is required to be identified or characterised. In particular, it is useful in relation to immunoblotting of proteins of high molecular weight, e.g. 150–250 kDa, in order to split them into fragments in which epitopes can be recognised by immunoblotting.

The first stage of the method of the invention comprises digestion of the proteins within the same gel as that on which they were separated. Within this stage, there are preferably three main operations. The first operation is to dehydrate the gel. The gel may be fully or partially dehydrated depending on the amount of protein digestion required. The greater the dehydration the greater the capacity of the gel subsequently to absorb a solution containing the first polypeptide-cleaving reagent and therefore the greater the digestion. Dehydration may be complete, substantially complete, e.g. by removal of 90–99% by weight of the original water content, or, more preferably, partial, e.g. by removal of 25–90%, preferably 40–70%, on the same basis. Of course, it is more troublesome to rehydrate a completely dried-out gel. The method of dehydration is not critical. Air-drying at ambient temperature, say 15–25° C. is preferred. Mere standing of the gel at 4–10° C. under low pressure is another method. Air-drying, followed by standing, is a further method.

The next operations are rehydration and the incorporation of the first polypeptide-cleaving reagent in the rehydration buffer. The polypeptide-cleaving reagent is preferably an enzyme such as trypsin or Lys-C, but a chemical cleaving agent such as CNBr could alternatively be used. Examples of other enzymes and chemical cleaving reagents are given later, in connection with the discussion of the second polypeptide-cleaving reagent. Hereinafter enzymes will be referred to, the extrapolation to other polypeptide-cleaving reagents being taken as understood and incorporated mutatis mutandis in the following description. The first enzyme may be the same as or different from the second enzyme(s) used in the transblotting step. Any of the enzymes described below for use in transblotting can be used in the in full gel digestion.

In principle, it is immaterial at what stage the first enzyme is introduced into the gel and whether it is present in the gel in a free or immobilised form. However, if present in the gel from the start of electrophoresis, it would normally upset the pattern of protein separation, unless the enzyme or conditions of running the gel were so chosen as to make it inactive while the gel is being run. This could be achieved by adding a reversible inhibitor, of the enzyme to the running buffer. For example, if the enzyme is trypsin a reversible inhibitor such as benzamidine would be suitable. Conditions are e.g. as described in S. L. Jeffcoate et al., J. Clin. Endocrinal. Metab. 1974 38, 155–157. Then, after the gel has been run, resulting in separation of proteins, it is washed as part of the rehydration step, resulting in the removal of inhibitor and therefore re-activation of the enzyme.

The enzyme is normally added to the gel after isolation of the proteins. It is added as a solution or fine suspension which will penetrate the gel and be absorbed well by the gel solids. In principle, the enzyme could be added before any deliberate step of rehydration or even after rehydration has been effected, e.g. in a concentrated solution. However, in practice, such techniques are unlikely to give the best digestion. Normally, the enzyme will be present in the rehydration solution, which is buffered. Preferably the gel is incubated with the rehydration buffer containing the enzyme, for example for 30 minutes at 35° C. The time and temperature can be varied, according to the size of fragments desired. Rehydration may be partial, complete or even to an extent in which the gel contains more water than when the proteins were run on it. Any extent of rehydration appropriate to allow transblotting is permissible. In practice, it is convenient to treat the gel with excess rehydration solution and to remove the excess. Otherwise, undesired protein diffusion or excessive swelling of the gel can occur.

At this stage the gel contains peptides with a high number of missed cleavages, from partially digested proteins. The fragments of high molecular weight and basic proteins are more easily extractable from the gel by electroblotting, compared with the full molecule.

Figure 2:
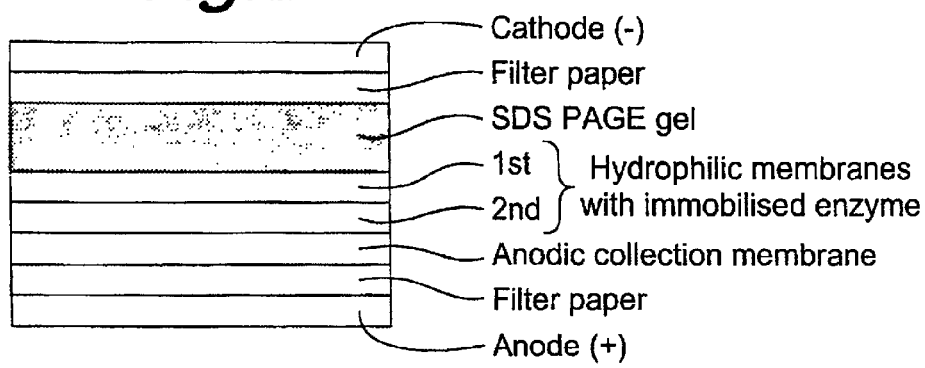
Figure 3:
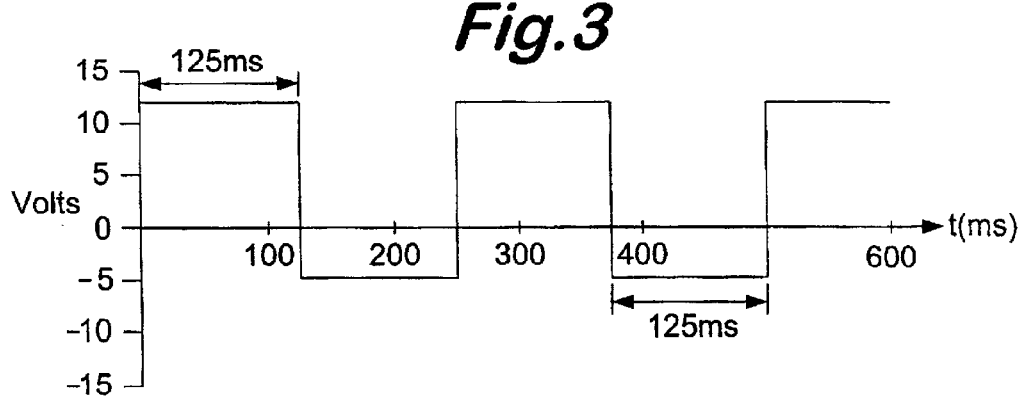
FIG. 3 is a plot of applied voltage against time, showing the production of an alternating voltage for use in electroblotting in the method of the invention.

The second stage of the method of the invention comprises transblotting, preferably electroblotting. Normally, the electroblotting takes place overall in the direction cathode to anode, as the proteins are negatively charged. Depending on the pH of the electroblotting buffer used, positively and negatively charged fragments could be obtained and migrate in opposite directions, towards the cathode and anode respectively. FIGS. 1 and 2 of the drawings exemplify some sandwiches for the electroblotting. FIG. 1 shows an experimental arrangement in which a cathodic collection layer, which is preferably a conventional PVDF membrane, was provided, just to show that under these conditions no proteins migrated to this membrane, despite the alternating field applied (thus reversing the electrodes). It will be understood that under different pH conditions, some fragments could be produced at the cathodic collection layer. Thus, the invention includes the possibility of providing anodic and cathodic collection layers, with hydrophilic membranes interposed between each of them and the separation gel layer. In FIG. 1 there is a single hydrophilic membrane, which is preferably a modified PVDF membrane, having an appropriate protein-cleaving reagent, normally a protease enzyme, for example trypsin, immobilised on it, interposed between the gel layer and an anodic collection layer, most conveniently a conventional PVDF membrane, on which the protein fragments are collected. In FIG. 2 there is no cathodic collection layer, but there are two consecutive hydrophilic membranes, preferably modified PVDF membranes, each with trypsin immobilised thereon, placed between the gel layer and the anodic collection layer, which, again, is preferably a conventional PVDF membrane.

In more detail, the anode and cathode are separated from the rest of the sandwich by an absorptive layer which soaks up the blotting liquid, while maintaining the liquid in electrical contact with the electrodes, and is conveniently a filter paper. The kinds of electrodes and absorptive layers used in arrangement are not critical and can be any conventionally used in electroblotting.

The anodic collection layer (and cathodic collection layer if used) are also not critical and thus can be any conventional hydrophobic membrane used in electroblotting, such as PVDF (conventional or positively charged) nylon or nitrocellulose, for example.

The "filling" of the sandwich can take the form of one or more membranes (defined as above) sufficiently hydrophilic in character that the proteins and fragments thereof do not tend to stick thereon. This membrane can be formed from any thin member which is porous to the electroblotting liquid and capable of immobilising the polypeptide-cleaving reagent thereon, whether on the surface thereof of within interstices or microcavities therein accessible to the electroblotting liquid (and therefore to the polypeptide to be cleaved). It will typically be from 100 to 600 $\mu$m thick. Usually the number of such membranes will be from 1 to 3. With conventional thicknesses of membrane, e.g. 130 to 150. Am as in the preferred "Immobilon AV" PVDF membrane, 2 membranes will frequently be used. They are best placed directly mutually adjacent, i.e. one on top of another. Preferably, the second polypeptide cleaving reagent is bonded to the hydrophilic membrane covalently. For this purpose, the hydrophilic membrane(s) are preferably provided with "active carbonyl" or carboxylic acid groups or derivatives thereof reactive with amino groups present in the cleaving reagent, e.g. an enzyme. "Active carbonyl"-modified or carboxyl-modified PVDF membranes are especially preferred.

Since it would be difficult to react all the active groups present on the surface of a membrane with an enzyme, and since it is undesirable to allow the polypeptides to react with these free active groups, the residual active groups (which would otherwise be free) are preferably capped before the membrane is used, e.g. with ethanolamine, thus providing terminations such as —CO—NH—CH$_2$—CH$_2$—OH, which are relatively hydrophilic. Other hydrophilic capping groups will suggest themselves to those skilled in the art.

Alternatively, PVDF membranes or glass fibre paper can be functionalised by isothiocyanate, which allows reaction with the N-terminal amino groups and/or the $\epsilon$-amino groups of lysine residues in the enzymes. For this purpose, the PVDF membranes are pre-treated with NaOH to provide a carbon-carbon ethylenic double bond in the polymer chain, by elimination of a molecule of HP. The pre-treated PVDF membranes are then reacted under basic conditions with a dinucleophile such as ethylenediamine, 1,10-diaminodecane or 2-aminoethanethiol, whereby hydrogen atoms in the polymer are substituted by —X—$(CH_2)_n$—$NH_2$ groups, wherein —X— is —S— or —NH— and n is 2 or 10. This polymer, having amine-terminated side-chains, is then reacted with 1,4-phenylenediisothiocyanate (DITC) or 3,5-dichloro-1,4-phenylenediisocyanate (DCDITC) to give the required isothiocyanate-terminated side-chains in good yield. DITC-reacted glass fibre sheets provide another form of membrane, see R. H. Aebersold et al., J. Biol. Chem. 1986, 291, 4229–4338.

Another form of hydrophilic membrane is PVDF functionalised by arylamine groups, which react with a carboxylic acid side-chain or the carboxyl terminus of the enzyme, preferably in the presence of a carbodiimide such as 1-(3-dimethylaminopropyl)-3-ethylcarbodimide.

Another form of hydrophilic membrane which can be used as the sandwich filling is a thin film or coating of agarose gel. The H-terminal amino and/or ε-amino groups (according to the selectivity of the reaction) of lysine residues in the enzyme are treated to obtain aminoxy groups, which react with aldehyde groups produced by mild oxidation of the agarose gel, thus bonding the enzyme covalently to the agaraose.

A further kind of hydrophilic membrane may comprise one or more thin films or coatings of polyacrylamide gel, similar in thickness to that used in immobilised pH gradient electrophoresis (IPG), but which has been trypsinated. This can be done by reacting trypsin with acryloyl chloride to form an N-acryloyltrypsin, which is then copolymerised with acrylamide in the preparation of an acrylamide copolymer gel.

Yet another form of hydrophilic Membrane is a glass fibre paper which has been modified to replace amino groups by groups containing a diazo linkage, e.g. 4-N,N-dimethylaminoazobenzene-4'-isocyanate groups. The reactions required for this purpose have been described by J. Y. Chang et al., FEBS Letters 1977, 84, 187–190.

The cleaving reagent immobilised on the membrane is normally and preferably immobilised by covalent bonding. However, other forms of immobilisation are not excluded from use in this invention, so long as the enzyme does not become sufficiently free in solution in the electroblotting liquid as to undergo autodigestion. (It will be understood that the presence of autodigested enzyme fragments could upset the analysis of the fragments from the protein to be analysed). Thus, for example, the enzyme could be physically trapped within the pores of a porous sheet of hydrophilic polymer. Alternatively, the membrane could have an enzyme immobilised thereon by means comprising (consisting of or including) affinity bonding. Thus, the enzyme could be covalently attached to avidin or streptavidin and the resultant conjugate attached to a biotinylated membrane by affinity bonding between avidin/streptavidin and biotin. Alternatively, avidin or streptavidin could be attached to the membrane and the enzyme could be reacted to provide biotinyl terminations for reaction with a membrane to which avidin or streptavidin has been attached.

Preferably either or both polypeptide-cleaving reagents comprise an enzyme. If both comprise an enzyme, it may be the same or different. Most preferably and usually, the enzyme cleaves the main chain of the polypeptide (i.e. is an endopeptidase or endoproteinase), especially trypsin.

Trypsin cuts proteins at the C-terminal end of many lysines and arginines. Other less specific endoproteases, e.g. pepsin or such as chymotrypsin are usable, as are highly specific enzymes such as Lys-C, Arg-C or Glu-C. For phosphoproteins, a phosphorylase is useful. Either or both enzymes can be an exo-enzyme which splits off a side-chain of the protein or acts at the terminus. More than one enzyme can be incorporated in the gel. More than one enzyme can be immobilised on the membrane. For example, it may be helpful to split off one or more side chains of the polypeptide, e.g. using a carboxypeptidase or aminopeptidase, in conjunction with an endoproteinase. Carboxypeptidase Y is one particularly useful such enzyme.

To investigate the presence of side-chains in proteins, such as glucosyl, N-acetyl-O-glucosaminyl and sialyl, enzymes which will cleave those chains, such as glucosidase, N-acetylglucosaminidase and neuraminidase, respectively, are useful in the invention.

The following chart indicates the various possibilities for types of enzymes which may be used in combination:

| IFG | OSDT |
| --- | --- |
| Endopeptidase, e.g. trypsin | Endopeptidase, e.g. trypsin |
| Endopeptidase, e.g. trypsin | Exo-enzyme, e.g. glucosidase, phosphorylase |
| Exo-enzyme, e.g. glucosidase, phosphorylase | Endopeptidase, e.g. trypsin |
| Exo-enzyme, e.g. glucosidase, phosphorylase | Exo-enzyme, e.g. glucosidase, phosphorylase |

The cleaving reagents are not confined to enzymes. Either or both can be a chemical reagent, for example cyanogen broumide, 2-iodosobenzoic acid or a derivative thereof or hydroxylamine. Such reagents are described by E. A. Carrey, "Peptide Mapping" in "Protein Structure: A Practical Approach", ed. T. E. Creighton, IRL Press, 1989, pages 117–121. For use as the second polypeptide-cleaving agent, the chemical reagents are suitably immobilised on the hydrophobic member. Thus, cyanogen bromide can be physically immobilised by entrapment within pores of the hydrophilic membrane. 2-iodosobenzoic acid can be derivatised, preferably at the COOH group, e.g. with an alkylenediamine, especially 1,6-hexanediamine, leaving a free amino group which is then reacted with functional groups on the membrane, such as active carboxyl groups mentioned above.

It will be appreciated that different cleaving reagents will have different specificities and in certain cases the absence of small fragments, indicating the absence of cleavage, may be a useful result for identification or characterization.

The electrical current applied in the electroblotting is preferably not a direct, continuous current, but either pulsed, i.e. a direct current with intervals in which no current is passed, or an alternating current. It may be unbiased or biased in the cathode to anode direction, i.e. mainly a cathode to anode current, but with intervals in which current is passed in the opposite direction. Variations on these regimes are possible within the general spirit of the idea of performing a slower than normal electroblotting, allowing sufficient time for the cleavage to take place on the hydrophilic membrane(s), while avoiding such a slow journey of the protein fragments from the separation gel to the collection membrane that lateral diffusion occurs, causing loss of resolution.

The electroblotting liquid is not critical to obtaining some form of protein fragmentation and hence a useful identification. It is normally buffered and can be any conventional buffer for this purpose, such as Tris/glycine with methanol or 3-(cyclohexylamino)-1-propanesulfonic acid (CAPS) with methanol. The direction of migration of the fragments depends essentially on the pH of the buffer. For most purposes an alkaline buffer will be appropriate, since many enzymes function best at alkaline pH. Particularly, in the case of trypsin, the buffer will preferably have a pH from 8.0 to 9.0 and most especially 8.2 to 8.6, with a half Towbin's buffer of pH about 8.4 being considered optimal. Some other enzymes, such as endoproteinase V8, require an acidic pH. Under such conditions, the fragments will migrate to the cathode.

It has been found desirable to incorporate a avail amount of a conventional detergent such as SDS in the buffer, to produce micelles (negatively charged aggregates).

The protein fragments, whether they are peptides derived from the main chain of the protein or are residues of a side-chain, are collected on the collection layer. They are then preferably analysed by a spectroscopic method based on matrix-assisted laser desorption/ionisation (MALDI) or electrospray ionisation (ESI). The preferred procedure is MALDI with time of flight (TOF) analysis, known as MALDI-TOF MS. This involves forming a matrix on the membrane, e.g. as described in the literature, with an agent which absorbs the incident light strongly at the particular wavelength employed. The sample is excited by UV, or IR laser light into the vapour phase in the MALDI mass spectrometer. Ions are generated by the vaporisation and form an ion plume. The ions are accelerated in an electric field and separated according to their time of travel along a given distance, giving a mass/charge (m/z) reading which is very accurate and sensitive. MALDI spectrometers are commercially available from PerSeptive Biosystems, Inc. (Frazingham, Mass., USA) and are described in the literature, e.g. M. Kussmann and P. Roepstorff, cited above.

In this invention, the above method is applied to the scanning of the fragments of many proteins at once. Thus, many proteins can be run simultaneously on a polyacrylamide gel, subjected to the method of the invention to produce an array of spots on the collecting membrane and the array analysed as follows. After the PVDF membrane or other hydrophobic collection layer has been stained, a piece of it will be cut and fixed on the MALDI-MS sample plate, e.g. with silicon grease. An organic matrix-foming reagent is added to the membrane on the sample plate and the sample is then air-dried to form the matrix. The sample plate is inserted in the MALDI-MS spectrometer. An automated movement of the sample plate from a first to a second position and subsequent positions, to align the laser with individual spots in the array, is arranged by computer program. At each position a MALDI-MS spectrum is generated, the spectral information collected in digital form and the data downloaded to the ExPASy database research program (PeptIdent).

It is then relatively simple to provide automated output of the results by using the ExPASy server, as at present used for MIDI-TOF MS and to generate the data in a form handleable by computers.

It will be evident, therefore, that the present invention has huge potential for the automated identification and/or partial characterisation of proteins, e.g. in proteomics research. In effect, the invention provides in this preferred embodiment a "molecular scanner" for this purpose.

Other techniques for improving the mass accuracy and sensitivity of the MALDI-TOP MS can be used to analyse the fragments of protein obtained on the collection membrane. These include the use of delayed ion extraction, energy reflectors and ion-trap modules. In addition, post source decay and MS—MS analysis are useful to provide further structural analysis. With ESI, the sample is in the liquid phase and the analysis can be by ion-trap, TOF, single quadrupole or multi-quadrupole mass spectrometers. The use of such devices (other than a single quadrupole) allows MS—MS or $MS^n$ analysis to be performed.

Still other methods of analysis comprise immunoblotting using monoclonal or polyclonal antibodies and phosphoimaging.

Optionally, other components may be included in the kit, especially any one or more of the following: matrix-forming reagent for MALDI-TOF, rehydration buffer, electroblotting buffer, collection layer(s), e.g. cationic membranes and PAGE materials. In the case of immunoblotting, the kit may further comprise one or more antibodies, especially a range of monoclonal antibodies. Kits as defined above, but further comprising any one, two or more of the above optional components are hereby specifically declared to be within the invention. All components of the kit may be supplied in separate containers, but packaged overall as a kit.

The following Examples illustrate the invention. The words "Immobilon", "Trans-Blot", "Trizma", "Tween" and "Voyager" are Trade Marks and/or Registered Trade Marks.

EXAMPLES

Materials and Methods

Chemicals. "Immobilon" type AV (IAV) membranes were purchased from Millipore (Bedford, Mass., USA). Acrylogel-PIP 2.6% C solution was purchased from BDH (Poole, England). Broad range SDS-PAGE standard PVDF membranes were purchased from Bio-Rad (Richmond, Calif., USA). Trifluoroacetic acid (TFA), "Trizma base" (Tris), 3-(cyclohexylamino)-1-propanesulfonic acid (CAPS) and trypsin (type IX from porcine pancreas, dialysed and lyophilised) were purchased from Sigma (St. Louis, Mo., USA). Acetonitrile (preparative HPLC grade), calcium chloride, ethanolamine, glycine and α-tosyl-L-arginine methyl ester (TAME) were purchased from Fluka (Buch, Switzerland).

12.5%, 2.6% C linear gel (home made). To produce a 12.5% T, 2.6% C linear polyacrylamide gel, crosslinked with PIP ("PIP"=N,N'-diacryloylpiperazine), 8 ml of Acrylogel-PIP 2.6% C stock solution were mixed with 5 ml of Tris-HCl 1.5 M pH 8.8 and 6.6 ml of deionized water The polymerisation of the gel was induced with 20 μl of TEMED and 100 μl of APS (10% w/v). The solution was degassed and loaded into a Bio-Rad mini-2D gel support. To preserve the gel from the atmosphere, 0.5 ml of water-saturated sec-butanol was added on the top of the gel. After 30 minutes, the gel was washed for subsequent loading of the 4% stacking gel. It was obtained from the mixture of 2.6 ml Acrylogel-PIP 2.6% C stock solution, 5 ml of Tris-HCl 1.5 M, pH 8.8, 12.3 ml of deionised water, 20 μl of TEMED and 100 μl of APS (10% w/v). The solution was degassed and loaded on top of the gel. A comb was inserted before gel polymerisation to create 15 sample wells. The gel can be used directly after 30 minutes of polymerisation.

1-D PAGE. For the 1-D PAGE method, Mini-Protean II electrophoresis apparatus (Bio-Rad, Richmond, Calif., USA) was used. SDS-PAGE was conducted essentially according to the method of Laemmli, with 12.5% T, 2.6% C polyacrylamide gel. The protein samples used were Bio-Rad SDS-PAGE standards. They were bovine pancreatic trypsin inhibitor (6.5 klDa), chicken lysozyme (14.3 kDa), soybean trypsin inhibitor (20.1 kDa), bovine carbonic anhydrase (28.9 kDa), chicken ovalbumin (42.7 kDa), bovine serum albumin (66.4 kDa), and rabbit phosphorylase b (97.2 kDa), *E. coli.* β-galactosidase (116.4 kDa) and rabbit myosin (about 200 kDa). Protein migration was carried out on a single lane at 200 V for 40–50 minutes.

Covalent attachment of tzypsin and blockage of the IAV membrane. IAV membrane is a commercially available modified PVDF membrane, having activated carboxylated groups. These groups are reactive towards nucleophiles such as amine groups from proteins or peptides. Based on the above-cited Millipore technical documentation on "Immobilon AV", trypsin was immobilised on this membrane (FIG. 1).

A 10×12 cm IAV membrane was incubated in a rotating hybridiser HB-2D (Techne, Cambridge, England) with 20 ml of a 2.5 mg/ml trypsin solution in 20 mM sodium dihydrogen phosphate buffer, pH 7.8, at room temperature for 3 hours. Then, the membrane was washed 3 times rapidly and vigorously with 20 ml of PBS-"Tween" 20 solution (20 mM of sodium dihydrogen phosphate, 140 mM sodium chloride and 0.5% "Tween" 20, pH 7.4) to remove unreacted trypsin. The membrane was incubated for 3 hours with 20 ml of 1M ethanolamine in 1M sodium bicarbonate, pH 9.5, at 4° C. to block the remaining active carboxyl groups of the membrane. After this capping step, the membrane was washed 3 times rapidly and vigorously with 20 ml of the PBS-"Tween" solution and then twice for 30 minutes with 20 ml of the PBS-"Tween" solution. The membranes were stored at 4° C. in a 46 mM Tris-HCl, 1.15 mM calcium chloride, 0.1% sodium azide buffer solution, pH 8.1.

Activity measurement of the enzyme covalently bound to the IAV membrane. The tryptic activity of the IAV-Trypsin membrane was determined using the trypsin assay reagent TAME. One to 2 cm² of the IAV-trypsin membrane was immersed in a mixture of 2.6 ml of 460 mM Tris-HCl, 11.5 mM calcium chloride, pH 8.1, 0.3 ml of 10 mM TAME solution and 0.1 ml of 1 mM HCl solution. After 40 seconds of vigorous stirring, the absorbance of the solution was measured at 247 nm with a UV-Visible spectrophotometer (Ultrospec III, Pharmacia Biotech, Uppsala, Sweden). A second measurement was made after 3 minutes of constant stirring. The equivalent amount of free active trypsin per surface unit was calculated from the change per minute in optical absorbance at 247 nm.

In full gel (ZFG) protein digestion and conventional electroblotting (for comparison). Immediately after the SDS-PAGE protein separation, the gels were soaked 3 times in deionised water for 5 minutes to eliminate SDS, glycine and Tris. The entire wet gel or a selected part of it was air dried at room temperature during 8 hours or overnight. The gel was rehydrated and incubated at 35° C. for 30 minutes with 3–5 times the initial volume of the gel of a solution of 0.05 mg/ml trypsin in 10 mM Tris-HCl, pH 8.2. The excess of trypsin solution was removed. Then, the gel was incubated for a further 30 minutes at 35° C. to complete the digestion. Proteins and peptides contained in the gel were electroblotted onto PVDF membranes using standard procedure with CAPS buffer, pH 11, 0.01% SDS in the tank.

One-step digestion transfer (OSDT) electroblotting (for comparison). Immediately after the SDS-PAGE protein separation, gels were soaked 3 times in deionized water for 5 minutes, and then equilibrated for 15 minutes in half Towbin's buffer (13 mM Tris, 100 mM glycine, 0.01% SDS. 10% methanol, pH 8.3). Electroblotting was carried out in half Towbin's buffer in a laboratory-made semi-dry apparatus. [Note: the "semi-dry" method is well known, see e.g. P. R. Fausset and B. S. Lu, Electrophoresis 1991, 12, 22–271.] It was carried out for 16 hours at room temperature (21 to 24° C.), with a square-shape alternating applied voltage, periodically +12.5 V for 125 ms and −5 V for 125 ms. The shape of the applied voltage is shown in FIG. 3, in which voltage is plotted on the y-axis and time in milliseconds on the x-axis. The average effective voltage $U_{eff}$=3.75V and is given by the identity $$U_{eff} = \frac{1}{T} \times [\text{Integral between } 0 \text{ and } T \text{ of } Udt]$$

where U is the voltage at a particular timepoint, dt is the change in time between the limits of the integration and T is the total time of one cycle or period=250 ms.

To perform the enzymatic digestion of the protein during the electroblotting, a double layer of IAV-trypsin membrane was placed between the polyacrylamide gel as a protein source and the PVDF membrane as the collecting surface to create a transblot-digestion sandwich (FIGS. 1 and 2).

After the electroblotting transfer procedure, the PVDF collection membranes, i.e. on which the fragments of digested protein were collected, were washed in deionised water for 5 to 15 minutes. Proteins remaining in the gel after the electroblotting were stained with Coomassie Blue R250 (0.1% w/v), methanol (30% v/v) and acetic acid (10% v/v) for 30 minutes. Gels were destained by repeated washing with methanol (40% v/v), and acetic acid (10% v/v) solution. The PVDF collection membranes were stained with Amido Black (0.5% w/v), isopropanol (25% v/v) and acetic acid (10% v/v) for 1 minute and then destained by repeated washing with deionised water. The membranes were air-dried before optical scanning.

IFG/OSDT electroblotting (combined method of the invention). In the combined method, the IFG procedure was modified by allowing only the first 30 minutes for rehydration and partial protein digestion. The gel was then transblotted onto PVDF membrane using the OSDT process described above. The electroblot transfer was carried out in half Towbin's buffer containing 0.01% SDS, as described above.

MALDI-TOF equipment and experimental conditions. PVDF membranes were analysed with a MALDI-TOF mass spectrometer "Voyager" Elite (PerSeptive Biosystems, Framingham Mass., USA) equipped with 337 nm nitrogen laser. The analyser was used in the reflectron mode at an accelerating voltage of 18 kV, a delay of ion extraction of 100 ns and a low mass gate fixed at 850 Da. Laser power was set slightly above threshold for molecular ion production. Spectra were obtained by summation of 10 to 256 consecutive laser shots without any smoothing procedure. Small pieces of the PVDF (1×3 mm square) containing the stained protein were cut from the PVDF collection membrane and fixed on an adaptable sample MaLDI plate with silicon grease. For deposition of the matrix required for MALDI-TOF MS, 1 μl of 4 mg/ml α-cyano-4-hydroxycinnamic acid in 30% acetonitrile, 0.1% TFA solution was added to the anodic PVDF membrane. For the internal calibration, the matrix solution contained 20 nM and 100 nK respectively of two C-amidated synthetic peptides of molecular weights 1498.82 Da and 2095.08 Da. Treatment of spectra and use of software.

Detected peaks were submitted to the peptide mass fingerprint search tool "PeptIdent" available on the World Wide Web (http://www.expasy.ch/www/tools.html) located at the ExPASy server (http://www.expasy.ch). No pI limits were introduced to restrict the search. The apparent migration masses given by the Bio-Rad technical information sheet were used as a restricted condition on the mass value with an error of 20%, as well as the specie origin of the protein. Mass tolerance was ±0.2 Da.

Fragment masses were submitted to "FindMod" (http://www.expasy.ch/www/tools.html) to identify the amino acid sequence of fragments from their spectral molecular weights. FindMod has options to take into account possible cysteine and mothionine modifications of proteins.

Results

Trypsin was attached covalently to IAV membranes with a surface enzyme density, as determined by TAME test, of 0.6 to 1.2 $\mu$g of active trypsin per cm$^2$. The activity of the trypsin-bound IAV membranes remained stable when they were stored in the Tris-HCl/CaCl$_2$/NaN$_3$ solution at 40° C. for periods up to a month. Tryptic activity decreased slightly after use of the membrane in the method of the invention, but not sufficiently to impair its re-use in another experiment.

After SDS-PAGE separation, the nine proteins specified above, were run on the same track in the SDS-PAGE, were subjected to a control electroblotting plus three different digestion techniques:

Control electroblotting of the proteins in the tank method, without digestion, using the standard CAPS buffer, pH 11, IFG digestion followed by electrotransfer using the tank method with CAPS buffer, OSDT digestion through IAV membrane using a semi-dry method and the half Towbin's buffer, pH 8.3, Combined method of the invention (partial IFG followed by OSDT).

FIGS. 4A to 4D show the transblot pattern of the four Amido Black stained PVDF membranes corresponding to a control without digestion (A), IFG digestion (B), OSDT (C) and the combined method of the invention (D), with the molecular weights of the nine proteins indicated. FIGS. 5A to 5D show the pattern of the proteins remaining on the SDS gel.

Figure 4:
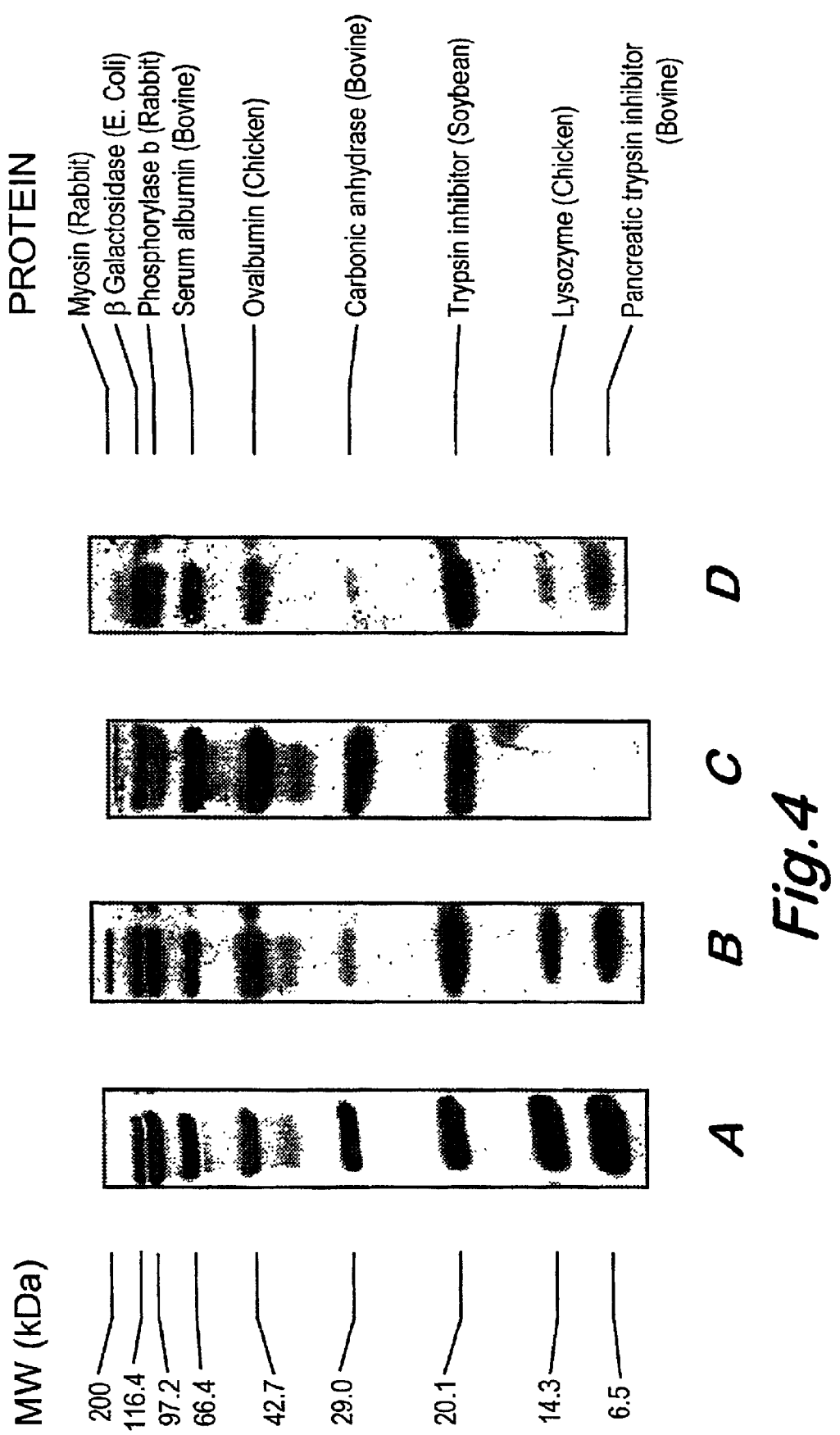
FIGS. 4A–4D and 5A–5D show stained polypeptide bands present on the collection membrane to which the proteins and protein fragments have been transferred, respectively, for control (4A, 5A), IFG digestion (4B, 5B), OSDT (4C, 5C) and the combined method of the invention (4D, 5D)
Figure 5:
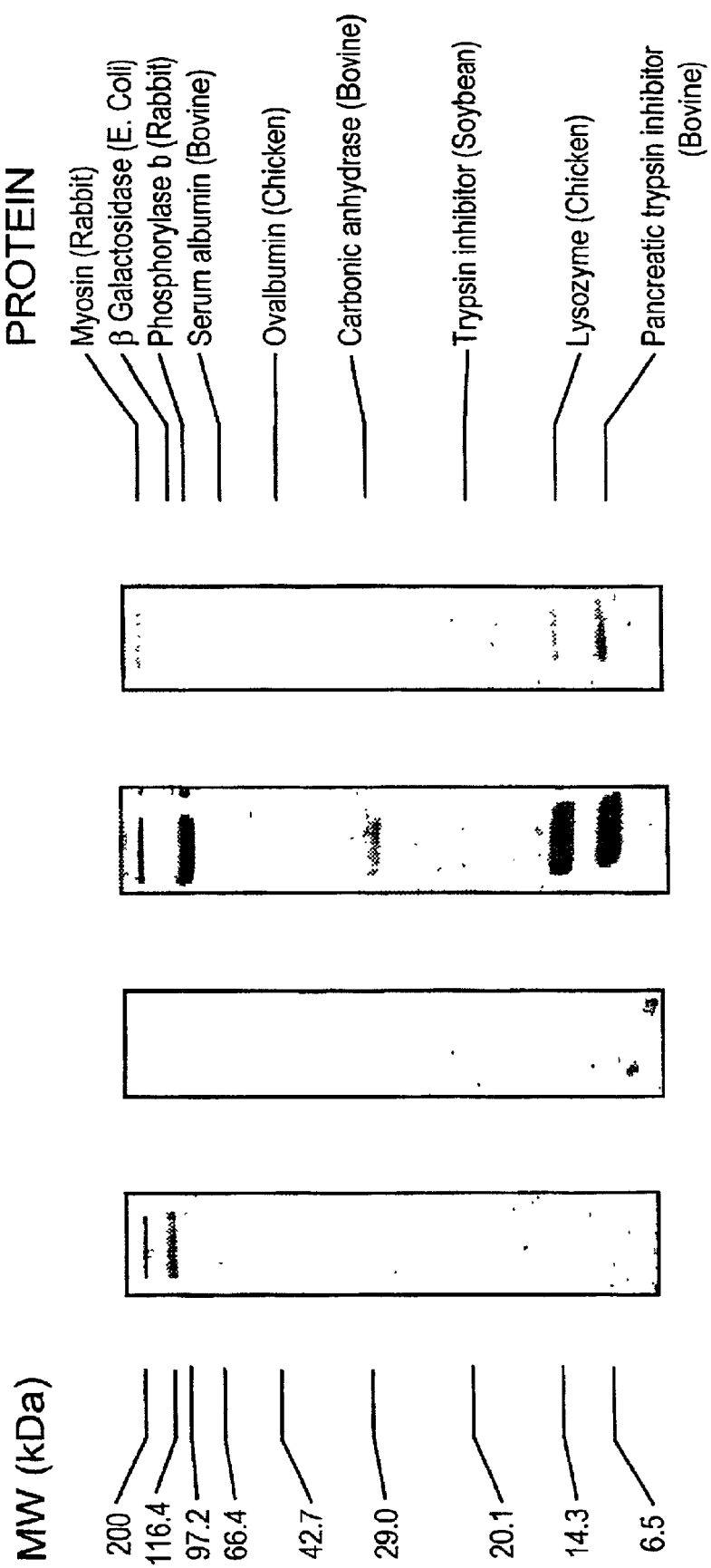

First, protein transfer using OSDT with half Towbin's buffer, 0.01% SDS, pH 8.4 (FIG. 4C) can be compared with the standard transfer using CAPS buffer, 0.01% SDS, pH 11. (FIG. 4A). Despite the addition of SDS in the ½ Towbin's buffer, basic proteins such as pancreatic trypsin inhibitor (pI 9.2) and lysozyme (pI 9.3) did not transfer. The influence of the SDS in the buffer was more noticeable for higher molecular weight proteins such as phosphorylase b (97.2 kDa) and myosin ($\approx$200 kDa) (FIGS. 4A and 4C). However, large amounts of these proteins remained in the gel after the electroblot (FIGS. 5A and 5C).

In the case of the IFG digestion (FIG. 4B) and the combined method (FIG. 4D), the PVDF membrane exhibited all of the 9 protein bands. PVDF patterns were similar to the normal transfer (FIG. 4A). The major difference between these PVDF membranes was that the intensity of the polypeptide beads was higher for normal protein transfer (FIG. 4A) and lower for the combined method (FIG. 4D). This should not be interpreted that the combined method of the present invention provided an inferior result as it should be noted that the digestion of proteins can modify their staining properties. Proteins remaining in the gel were very low in both IFG and combined methods (FIGS. 5B and 5D).

In a second experiment, these samples were analysed with MALDI-MS for peptide mass fingerprinting detection.

Figure 6A:
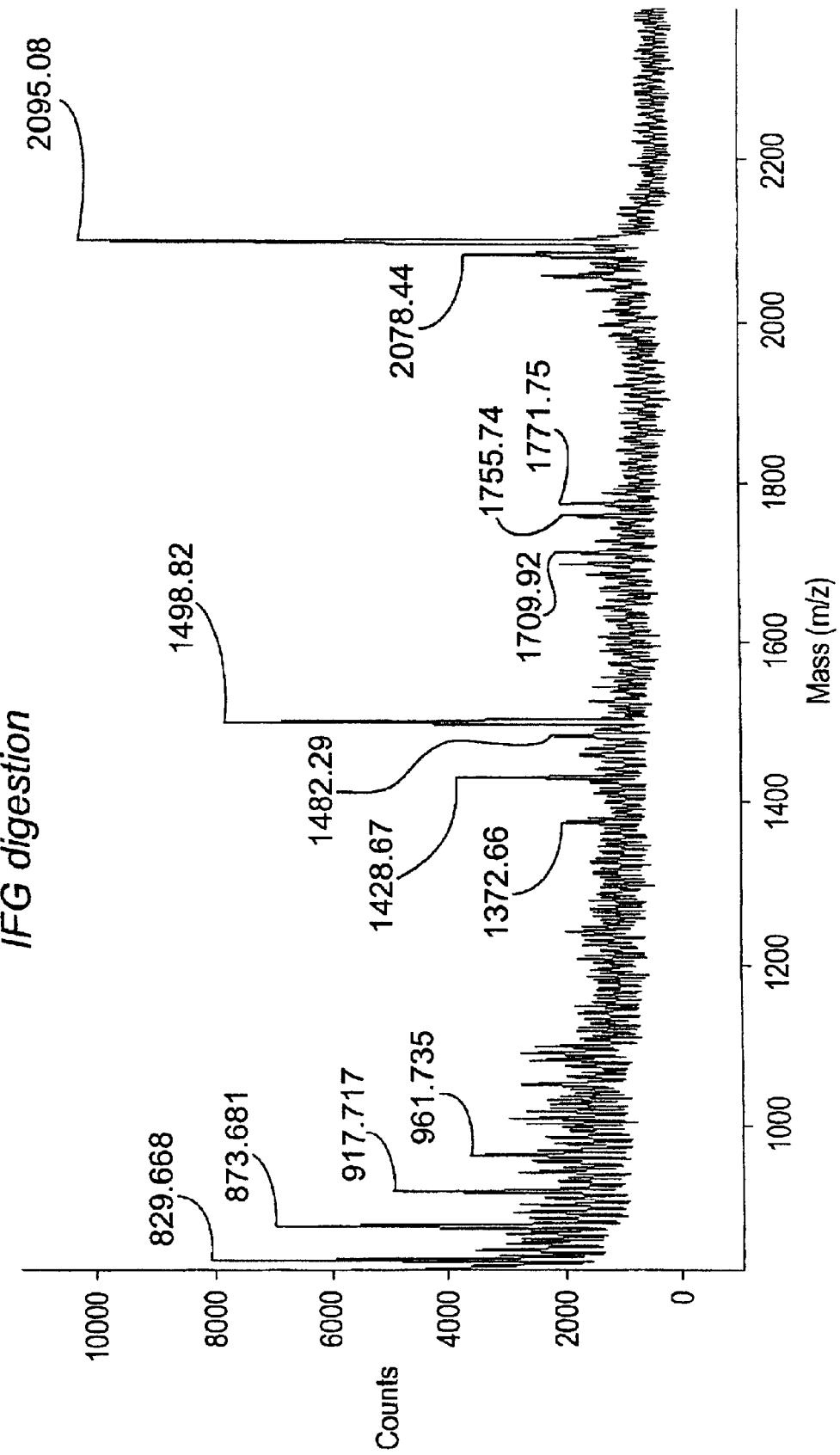
Figure 7A:
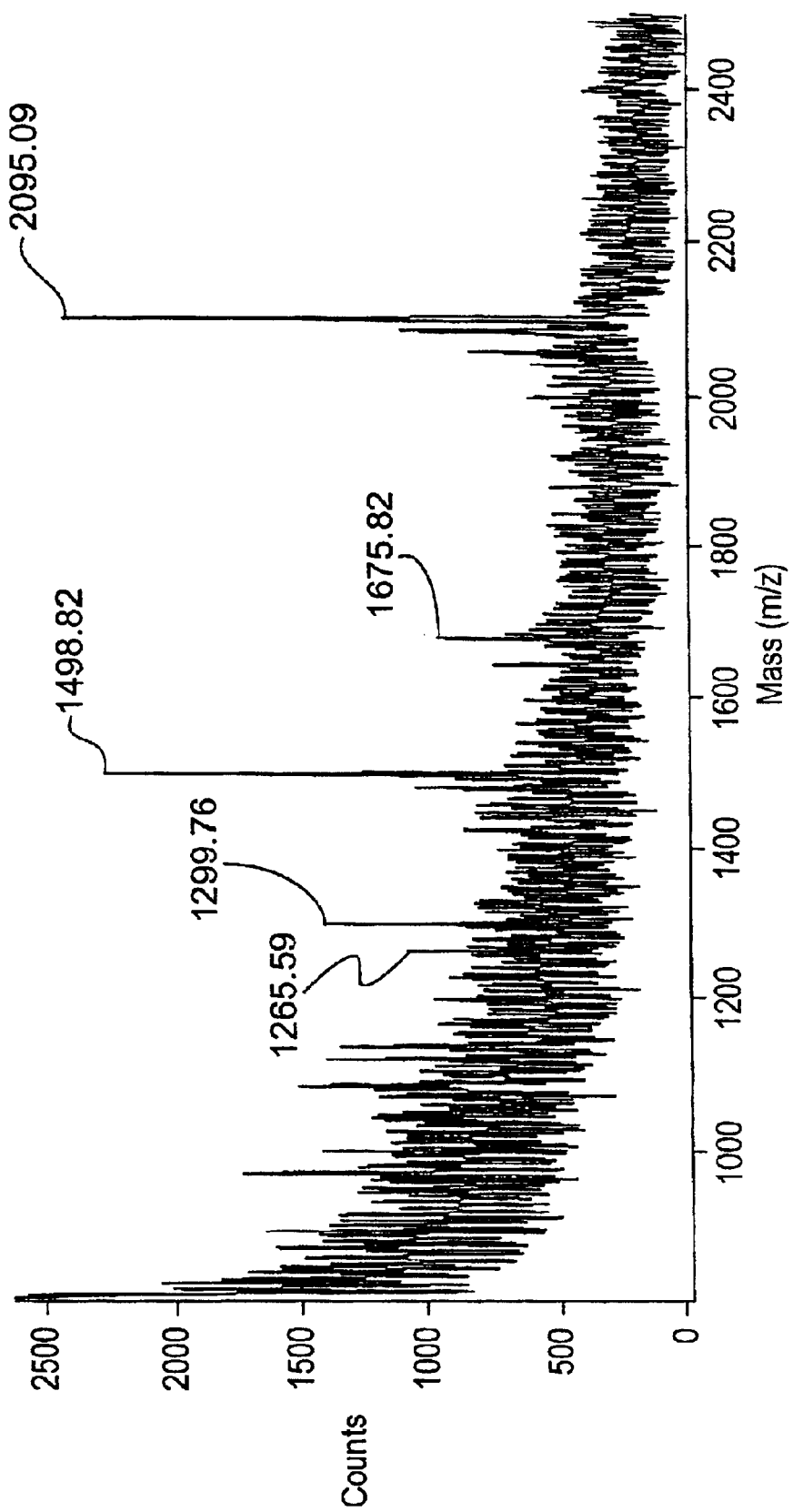
Figure 7B:
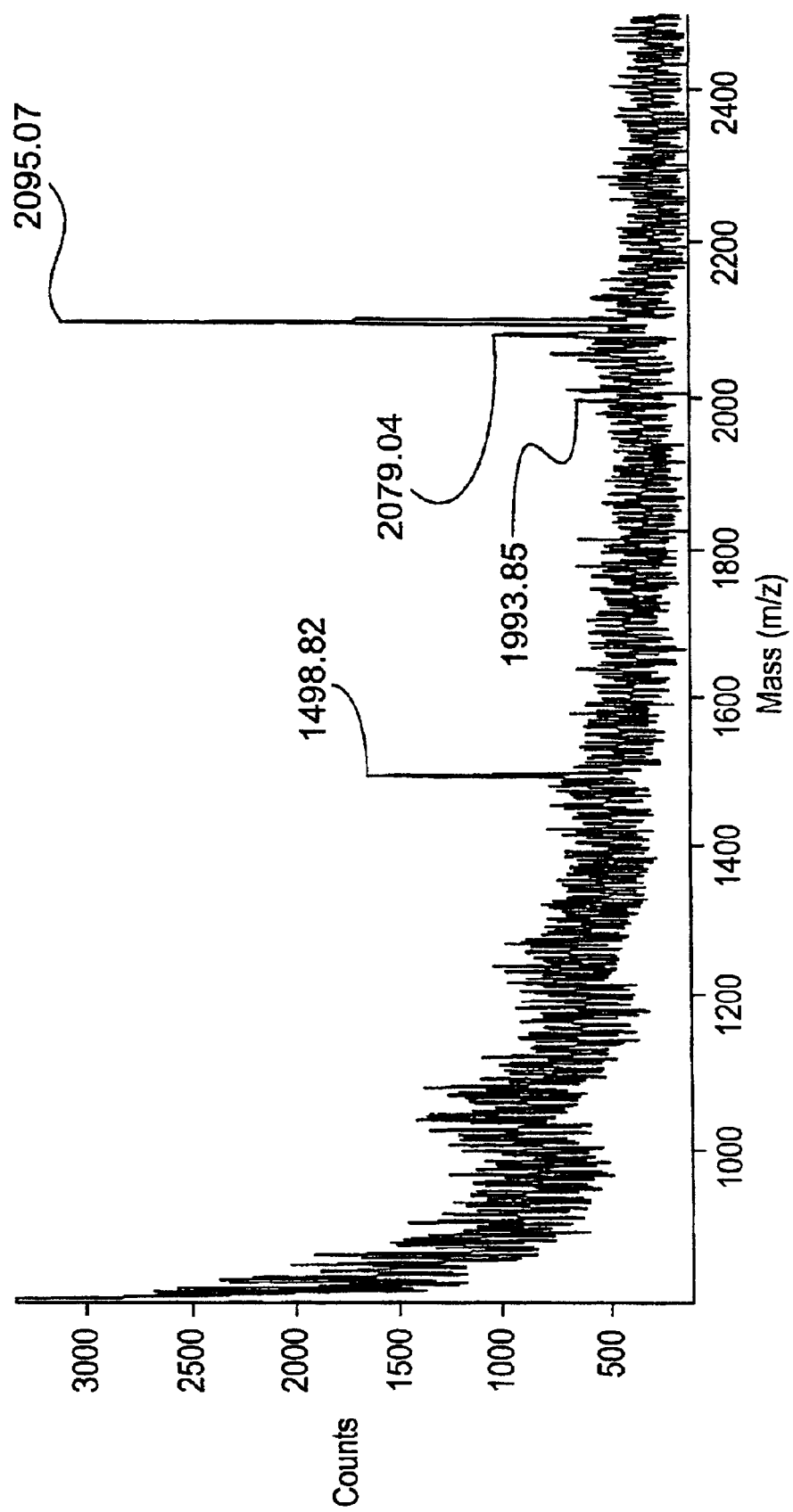
Figure 7C:
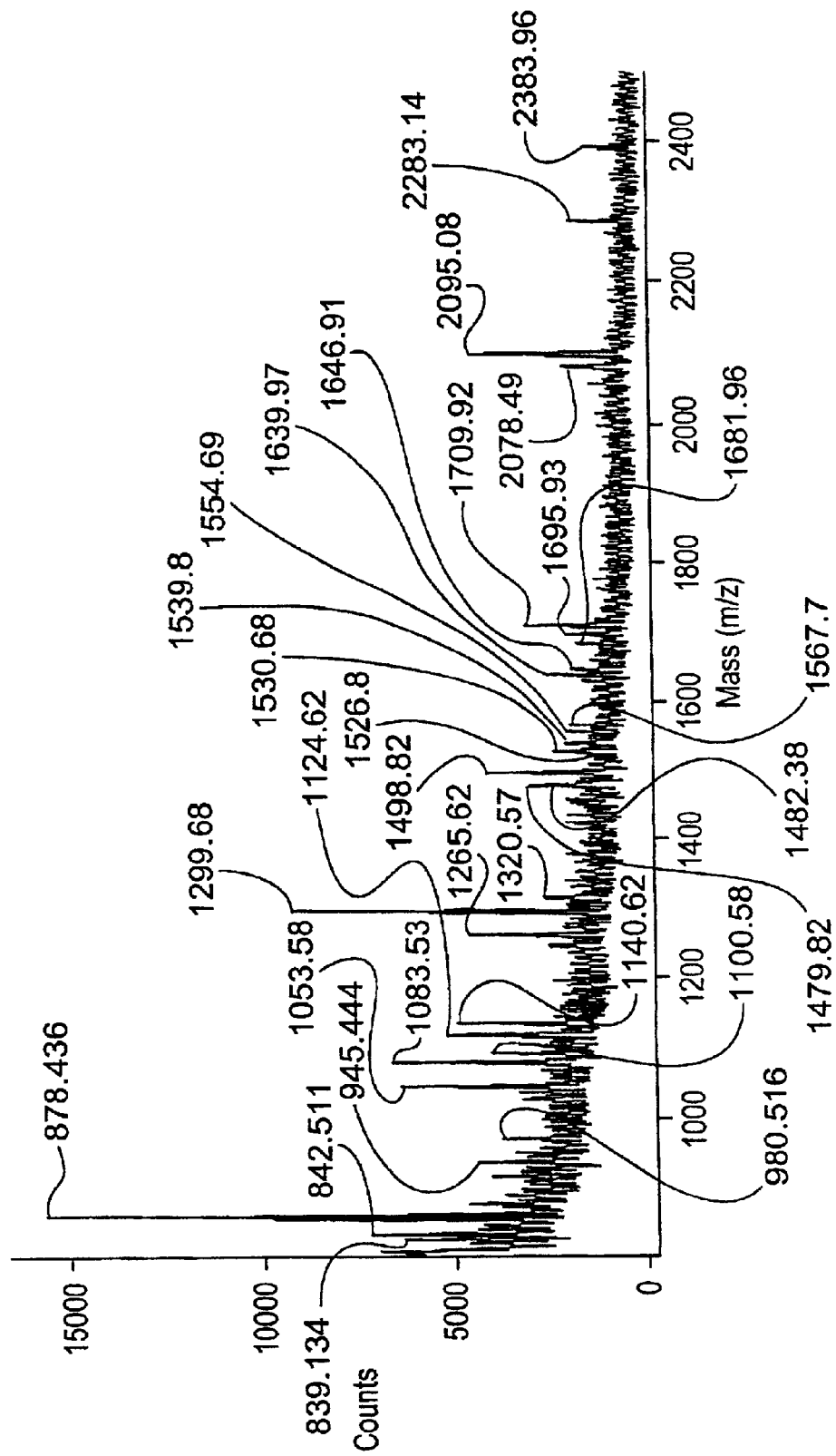

The results of these tests are summarised in Table 1. Recent results based on the OSDT process had previously highlighted the problems pointed out above, relating to partial transblot of basic and high molecular weight proteins. In this case, no identification could be obtained for lysozyme (pI 9.2) and pancreatic trypsin inhibitor (pI 9.3) as well as myosin (MW $\approx$200 kDa). The IFG digestion technique was not sufficient to obtain enough peptides to identify correctly most of the proteins. The combination method of partial IFG followed by OSDT provided overall the best results in terms of protein identification. All of the 9 proteins were identified and that despite the high pI of a lysozyme (see MALDI-MS spectra in FIGS. 6A–6C) and high molecular weight of a myosin (see MALDI-MS spectra in FIGS. 7A–7C) of the analysed proteins. FIGS. 6A, 7A relate to OSDT, 6A, 7B to IFG digestion and 6C, 7C to the combined method of the invention. Note in the combined procedure the greater number of fragments generated and the greater fragmentation of the marker proteins of m.w. 1498.82 and 2095.08 used for internal calibration.

TABLE 1

| | | | OSDT | | IFG | | Combined | |
|---|---|---|---|---|---|---|---|---|
| Protein name | pI[1] | MW (kDa)[1] | No. Pept[2] | Prot Id[3] | No. Pept[2] | Prot Id[3] | # of Pept[2] | Prot Id[3] |
| Bovine pancreatic trypsin inhibitor | 9.24 | 6.5 | 0 | – | 1 | – | 4 | + |
| Chicken lysozyme | 9.3 | 14.3 | 0 | – | 2 | – | 7 | + |
| Soybean trypsin inhibitor | 4.6 | 20.1 | 7 | + | 1 | – | 7 | + |
| Bovine carbonic anhydrase | 7.9 | 29.0 | 9 | + | 0 | – | 4 | + |
| Chicken ovalbumin | 5.2 | 42.8 | 7 | + | 4 | – | 5 | + |
| Bovine serum albumin | 5.6 | 66.4 | 4 | + | 3 | – | 12 | + |
| Rabbit Phosphorylase b | 6.8 | 97.2 | 12 | + | 1 | – | 17 | + |
| E. coli β-Galactosidase | 5.3 | 118.1 | 20 | + | 7 | + | 19 | + |
| Rabbit myosin[4] | — | 223 | 0 | – | 2 | – | 10 | + |
| % Identification | — | — | — | 67% | | 11% | | 100% |

[1]pI and molecular weight were calculated with the "Compute pI/Mw" tool (available on the ExPASy server)
[2]Number of peptides identified that correspond to correct enzymatic residue-specific fragments of the protein under test (determined with FindMod tool)
[3]+/–: Correct/incorrect identification of the protein using the peptide mass fingerprints obtained from MALDI-MS spectra, as determined by PeptIdent (Available on the ExPASy server)
[4]Myosin was correctly identified from rabbit skeletal muscle, using the TREMBL database Thus, it has been shown that the method of the present invention can identify proteins having a wide range of pI value and molecular weight. First, trypsin digested proteins in the gel without restriction of mass and/or pI. This step resulted in peptides of high average molecular weight corresponding to several missed cleavage, but their lower molecular weights were lower than that of the original protein. For a few peptides, pI and hydrophobicity were also lower than for the entire protein. Secondly, these peptides were easily extracted by electroblotting and digested again during the OSDT procedure. The method gave good mass spectra and subsequent identification for 9 out of 9 analysed proteins.

The myosin protein referred to above cannot be immunoblotted by conventional Methods, even when using CAPS buffer with 0.01% SDS. However, it can be immunoblotted by the above-described transblotting procedure. By use of a monoclonal antibody, myosin can be detected on the PVDF membrane.

Each of the above-mentioned publications is herein incorporated by reference to the extent to which it is relied on herein.

What is claimed is:

1. A kit comprising:
   a) a first polypeptide-cleaving reagent suitable for incorporating in an electrophoretic gel on which at least one polypeptide has been isolated by electrophoresis, said first polypeptide-cleaving reagent being capable of cleaving said polypeptide to produce a partially cleaved polypeptide;
   b) at least one hydrophilic membrane capable of use in transblotting said partially cleaved polypeptide from said electrophoretic gel, the membrane having at least one second polypeptide-cleaving reagent immobilised thereon, said second cleaving reagent being capable of further cleavage of said partially cleaved polypeptide to produce polypeptide fragments; and
   c) a hydrophobic collection member suitable for receiving thereon said polypeptide fragments from said hydrophilic membrane when transferred thereto by transblotting.

2. The kit of claim 1, wherein the hydrophilic membrane and hydrophobic collection member are provided as a preformed assembly.

3. The kit of claim 1 or 2, wherein the second polypeptide-cleaving reagent is immobilised on the hydrophilic membrane by covalent bonding.

4. The kit of claim 3, wherein the second polypeptide-cleaving reagent is immobilised through an amide linkage formed between (1) functional groups on the hydrophilic membrane selected from the group consisting of activated carbonyl groups, carboxylic acid groups and carboxylic acid derivative groups capable of reacting with an amino group, and (2) an amino group of the polypeptide-cleaving reagent.

5. The kit of claim 1 or 2, wherein the polypeptide-cleaving reagents are enzymes, which may be the same or different.

6. The kit of claim 5, wherein each enzyme comprises a protease.

7. The kit of claim 6, wherein the protease comprises trypsin.

8. The kit of claim 1 or 2, further comprising:
   d) a buffer suitable for at least partially rehydrating said electrophoretic gel on which at least one polypeptide has been isolated and which has been dehydrated.

9. The kit of claim 1 or 2, wherein the hydrophobic collection member is a self-supporting membrane.

10. A method of identifying or characterising polypeptides which have been isolated on a gel by electrophoresis, comprising the steps of:
    a) providing an electrophoretic gel on which at least one polypeptide has been isolated by electrophoresis;
    b) incorporating a first polypeptide-cleaving reagent in the gel, said cleaving reagent being capable of cleaving said isolated polypeptide contained by said gel to produce a partially cleaved polypeptide;
    c) providing adjacent to the gel at least one hydrophilic membrane on which is immobilised at least one second polypeptide-cleaving reagent capable of cleaving said partially cleaved polypeptide to produce polypeptide fragments;
    d) providing a hydrophobic collection member suitable for receiving thereon said fragments of polypeptide transferred thereto from said hydrophilic membrane by transblotting, said hydrophobic member being positioned beyond the hydrophilic membrane in a direction of movement of the fragments of polypeptide;
    e) partially cleaving the isolated polypeptide on the electrophoretic gel by the first polypeptide-cleaving reagent to produce a partially cleaved polypeptide, transblotting the partially cleaved polypeptide from the electrophoretic gel through the hydrophilic membrane under conditions effective to cause it to be further cleaved into polypeptide fragments by the second polypeptide-cleaving reagent, and transblotting the polypeptide fragments onto the hydrophobic collection member; and
    f) identifying or characterising the polypeptide fragments collected on the hydrophobic collection member.

11. The method of claim 10, which further comprises:
    g) identifying or characterising the isolated polypeptide from which the polypeptide fragments were derived.

12. The method of claim 10 or 11, wherein the first polypeptide-cleaving reagent is incorporated in the electrophoretic gel by dehydrating the electrophoretic gel and then at least partially rehydrating it with a buffer containing the polypeptide-cleaving reagent.

13. The method of claim 10 or 11, wherein the immobilisation of the second polypeptide-cleaving reagent is by covalent bonding thereof to the hydrophilic membrane.

14. The method of claim 10 or 11, wherein both the polypeptide-cleaving reagents arc enzymes, which may be the same or different.

15. The method of claim 14, wherein either or both enzymes cleave the polypeptide in its main chain.

16. The method of claim 14, wherein either or both enzymes cleave the polypeptide in a side-chain thereof.

17. The method of claim 14, wherein both enzymes are trypsin and the transblotting is carried out in a buffer of pH from 8 to 9.

18. The method of claim 10 or 11, wherein the transblotting is carried out at a voltage which is adjusted to provide a slower than normal transfer through said hydrophilic membrane so as to extend the residence time of the polypeptide in the proximity of the second cleavage reagent.

19. The method of claim 10 or 11, wherein the transblotting is carried out under conditions which provide either (1) a discontinuous current from anode to cathode or (2) an alternating current from the anode to cathode direction.

20. The method of claim 10 or 11, wherein the polypeptide fragments are identified by mass spectrometry.

21. The method of claim 20, wherein the membrane is scanned directly by matrix-assisted laser desorption/ionisation time of flight spectrometry and the data obtained therefrom compared with a database, using a computer program, to provide automated polypeptide identification of said isolated polypeptide.

* * * * *